United States Patent [19]

Steinke et al.

[11] Patent Number: 5,190,875
[45] Date of Patent: Mar. 2, 1993

[54] PEPTIDE AMIDASE AND THE USE THEREOF

[75] Inventors: Doerte Steinke, Aachen; Maria-Regina Kula, Niederzier-Hambach; both of Fed. Rep. of Germany

[73] Assignees: Forschungszentrum Juelich GmbH, Juelich; Degussa Aktiengesellschaft, Frankfurt am Main, Fed. Rep. of Germany

[21] Appl. No.: 694,981

[22] Filed: May 6, 1991

[30] Foreign Application Priority Data

May 7, 1990 [DE] Fed. Rep. of Germany ....... 4014564

[51] Int. Cl.$^5$ .................. C12N 9/78; C12N 9/80; C12N 9/82; C12N 9/84
[52] U.S. Cl. .................... 435/227; 435/228; 435/229; 435/230
[58] Field of Search ............... 435/227, 228, 229, 230

[56] References Cited

FOREIGN PATENT DOCUMENTS 0334358 3/1989 European Pat. Off. .
3629242A1 3/1987 Fed. Rep. of Germany .

OTHER PUBLICATIONS

Kula (Jul. 18, 1991) DE 4014564 in Chem. Abst., 116(7), Abst. #54611.
Zuber, H., "Reiningung und Eigenschaften der Carboxypeptidase aus Citrusfruchten", Hoppe Seyler's Z. Phys. Chem., 349:1337–1352, (1986).
Steinke et al., "Application Of Carboxypeptidase C For Peptide Synthesis", Enx. Microb. Techol., 12:836–840, (1990).
Breddam, K., "Chemically Modified Carboxypeptidase Y With Increased Amidase Activity", Carlsberg Res. Commun., 49:535–554, (1984).

*Primary Examiner*—Douglas W. Robinson
*Assistant Examiner*—Jon P. Weber
*Attorney, Agent, or Firm*—Foley & Lardner

[57] ABSTRACT

A peptide amidase isolated from the flavedo of citrus fruits, preferably oranges, which is capable of catalyzing the selective hydrolytic elimination of the free amino group on the C-terminal end of peptide amides but which does not cleave peptide bonds. The enzyme accepts D-amino acid residues in the C-terminal position, although the hydrolysis rate is much slower than with L-amino acid residues. The enzyme is weakly inhibited by serine protease inhibitors; has an optimal pH of 7.5±1.5, an optimum temperature of 30° C. at pH 7.5 and has an isoelectric point of pH 9.5. The peptide amidase is stable at pH 6.0–9.0. The molecular weight of the purified enzyme is 23,000 +/− 3000 daltons. A peptide amidase according to the present invention is particular useful in the production of peptides by continuous enzymatic reaction of N-protected amino acid or peptide alkyl esters with amides of amino acids. In the continuous reaction, the synthesized peptide amide is hydrolyzed by the peptide amidase and separated by anion exchange from the amide of the amino acid which can be recycled.

2 Claims, 5 Drawing Sheets

FIG. 7 Principle for a device for a dipeptide synthesis

SEQUENCE LISTING ( 1 ) GENERAL INFORMATION:

( i i i ) NUMBER OF SEQUENCES: 3

( v i ) CURRENT APPLICATION DATA:
        ( A ) APPLICATION NUMBER: US 07/694,981
        ( B ) FILING DATE: 06-MAY-1991

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( D ) TOPOLOGY: linear     ( i i ) MOLECULE TYPE: peptide     ( i x ) FEATURE:
        ( A ) NAME/KEY: Modified-site
        ( B ) LOCATION: 1..1
        ( D ) OTHER INFORMATION: /label=bzl
                / note="first aa is benzylated Cys"

( x i ) SEQUENCE DESCRIPTION: SEQ ID NO:1:

Cys Pro Arg Gly
    1

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:2:

Tyr Gly Gly Phe Leu
    1                     5

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:3:

Val Gly Ala Pro
    1

PEPTIDE AMIDASE AND THE USE THEREOF

This invention relates to an enzyme that is capable of catalyzing the selective hydrolytic elimination of the free amino group on the C-terminal end of peptide amides by the following reaction:

where:
- $R_x$ and $R_1$ are any side group (including $R=H$) of a natural or unnatural amino acid, and the side group can be protected or unprotected;
- $R'$ is a protective group when $n=0$; when $n>0$, $R'$ is a protective group or a hydrogen; and $n=$zero or any integer.

In addition, the hydrogen atoms in the 600 position of the individual amino acid residues can also be replaced by a lower alkyl group.

BACKGROUND OF THE INVENTION

Selective elimination of the C-terminal amino group of peptide amides is generally difficult to achieve by a chemical reaction because the peptide linkage is also subject to hydrolytic attack. Amidases which cleave amide group are known but these enzymes do not catalyze the cleavage of peptide amides and therefore, because of their α-amino acid amidase activity (DE-OS 36 29 242), can only be employed in the preparation of L-amino acids from α-unprotected amides of D,L-amino acids.

In addition to the foregoing amidases, peptidases which catalyze the hydrolytic cleavage of peptide linkages have merely a certain secondary activity for eliminating the C-terminal amino protective group are known. Carboxypeptidase Y is illustrative of these peptidases, especially in a chemically modified form (see K. Breddam, Carlsberg Res. Commun. 49 (1984) 535-54).

Accordingly, the enzymatic elimination of the free amino group of peptide amides without the simultaneous cleavage of peptide linkages has been considered infeasible heretofore.

SUMMARY OF THE INVENTION

Accordingly, it is an object of the present invention to provide a peptide amidase that is capable of catalyzing the selective hydrolytic elimination of the free amino group at the C-terminal location of peptide amides and is isolated from the flavedo of citrus fruits.

Another object of the present invention is to provide such a peptide amidase that is further capable of catalyzing the elimination of the C-terminal amino group of N-terminal protected amino acid amides.

A further object of the present invention is to provide a process for the production of peptides and amino acids with N-terminal protection having the general formula wherein $R'$ is a protective group or any amino acid or peptide residue attached by a peptide or isopeptide bond; $R_2$ is a hydrogen or alkyl and $R_1$ is a hydrogen or any side chain; and wherein a C-terminal amino group is removed from a peptide amide or an amino acid amide having N-terminal protection by reacting the peptide amide or the amino acid amide with such a peptide amidase.

Still a further object of the present invention is to provide a continuous process for the production of such peptides and amino acids.

In accomplishing the foregoing objectives, there has been provided, in accordance with one aspect of the present invention, in substantially pure form, a peptide amidase that is capable of catalyzing the selective hydrolytic elimination of the free amino group at the C-terminal location of peptide amides and is isolated from the flavedo of citrus fruits.

In accordance with another aspect of the present invention, a peptide amidase is provided that is capable of catalyzing the selective hydrolytic elimination of the free amino group at the C-terminal location of peptide amides and is isolated from the flavedo of oranges.

In accordance with still another aspect of the present invention, there has been provided, in substantially pure form, a peptide amidase as described above and that is further capable of catalyzing the elimination of the C-terminal amino group of N-terminal protected amino acid amides; (B) does not cleave peptide bonds; (C) has an optimum pH of 7.5±1.5; (D) is stable at pH 6.0-9.0; (E) has an optimum temperature of 30° C. at pH 7.5; (F) exhibits weak inhibition by serine protease inhibitors, particularly phenylmethanesulfonyl fluoride; (G) has a molecular weight of 23,000+/−3000 daltons as measured by electrophoresis; (H) has an isoelectric point of pH 9.5; and isozymes of the amidase. Aggregation of the 23000 daltons units may occur.

In accordance with a further aspect of the present invention, a process is provided for the production of peptides and amino acids with N-terminal protection having the general formula wherein $R'$ is a protective group or any amino acid or peptide residue attached by a peptide or isopeptide bond; $R_2$ is a hydrogen or alkyl and $R_1$ is a hydrogen or any side chain; and wherein a C-terminal amino group is removed from a peptide amide or an amino acid amide having N-terminal protection by reacting the peptide amide or the amino acid amide with a peptide amidase that is capable of catalyzing the selective hydrolytic elimination of the free amino group at the C-terminal location of peptide amides and is isolated from the flavedo of citrus fruits.

In accordance with yet a further aspect of the present invention, a continuous process is provided for the production of peptides and amino acids with N-terminal protection as described above.

In accordance with still a further aspect of the present invention, a process is provided for the production of peptides with or without N-terminal protection as described above wherein deamidation is carried out as process step in a coupled reaction with an enzyme selected from the group consisting of proteases, peptidases, esterases and lipases.

In accordance with another aspect of the present invention, a continuous process is provided for the production of peptides with or without N-terminal protection having the general formula wherein R' is a protective group or any amino acid or peptide residue attached by a peptide or isopeptide bond; $R_2$ is a hydrogen or alkyl and $R_1$ is a hydrogen or any side chain which optionally may be protected; and wherein a C-terminal amino group is removed from a peptide amide optionally having N-terminal protection by reacting the peptide amide with a peptide amidase that is capable of catalyzing the selective hydrolytic elimination of the free amino group at the C-terminal location of peptide amides and is isolated from the flavedo of citrus fruits and wherein the process comprises the steps of (A) reacting a compound selected from the group consisting of an optionally N-terminal protected amino acid alkyl ester and an optionally N-protected peptide alkyl ester with an amide of an amino acid in aqueous phase or in an aqueous-organic medium, in the presence of an enzyme that will catalyze peptide bonding with the resulting formation of a peptide amide; (B) reacting the peptide amide with the amidase to catalyze the elimination of an amide protective group from said peptide amide with the resulting formation of a peptide; (C) removing the peptide from the reaction mixture; and (D) recycling the amino acid amide used as the nucleophile.

In accordance with yet another aspect of the present invention, a continuous process is provided for the production of peptides and amino acids with N-terminal protection as described above wherein the peptide is removed from the reaction mixture and eluted chromatographically by anion exchange means and then may be converted it into its salt or hydrate.

In accordance with yet a further aspect of the present invention, a continuous process is provided as described above wherein the eluted peptide is converted into its salt or hydrate.

BRIEF DESCRIPTION OF THE DRAWINGS

In drawings which illustrate the embodiments of the invention.

DETAILED DESCRIPTION OF THE PREFERRED EMBODIMENTS

It has been discovered that a peptide amidase capable of catalyzing the elimination of the free amino group of peptide amides without simultaneously attacking peptide linkages can be isolated from the flavedo of citrus fruits. For the purposes of this invention, flavedo is defined as the outer colored layer of the exocarp of citrus fruit. A peptide amidase according to the present invention is capable of catalyzing the selective hydrolytic elimination of the free amino group on the C-terminal end of peptide amides. In addition, a peptide amidase according to the present invention can eliminate the C-terminal amino group of amino acids amides with N-terminal protection. In a preferred embodiment of the present invention, a peptide amidase is isolated from the flavedo of oranges.

In the naturally occurring mass of the citrus fruit flavedo, a number of other compounds, including, but not limited to, endo- and exopeptidases, such as carboxypeptidase C, are present in addition to a peptide amidase within the present invention. The presence of these additional compounds interfere with the biochemical synthesis catalyzed by the inventive peptide amidase and can lead to the decomposition of the desired end products of the synthesis. Accordingly, by isolating the inventive enzyme such interfering reactions are eliminated and the yield of the desired end products is increased. Moreover, isolation of the inventive enzyme also facilitates the recovery of the desired end products.

In substantially pure form, a peptide amidase according to the present invention has the following characteristics:

elimination of the C-terminal amino group of peptide amides and of amides of amino acids with N-terminal protection;
no cleavage of peptide bonds;
an optimal pH of 7.5±1.5;
good stability in a pH range of 6.0–9.0;
an optimum temperature of 30° C. at pH 7.5;
weak inhibition by inhibitors of serine proteases, especially phenylmethanesulfonyl fluoride;
a molecular weight of approximately 23000+/−3000 daltons as measured by electrophoresis;
an isoelectric point of pH 9.5.

A peptide amidase according to the present invention can be modified chemically or enzymatically by methods well known in the art or alternatively, can be in isozyme form.

A peptide amidase within the present invention exhibits selective enzymatic activity. The enzyme has neither peptidase activity nor amino acid amidase activity, as is evident from the results presented in Table 1 comparing the activities of a purified peptide amidase to carboxypeptidase Y in both its native and modified form.

TABLE 1

Comparison of the activity of peptide amidase and CPD-Y; Conditions for the determination of peptide amidase activity: 30 mM of different substrates, pH 9, 22° C., pH-stat

| | Peptide amidase | CPD-Y (native) | CPD-Y (modified) |
|---|---|---|---|
| Protein content (enzyme) in mixture [mg/mixture] | 0.038 | 0.75 | |
| Specific activity [U/mg protein] | 2-100 | 0.0082 | |
| Amino-acid amidase activity | no | yes* 0-92% | yes* 0-77% |
| Peptidase activity | no | yes | yes, but reduced |

*Strength varies depending on the amide of the amino acid.

For the purposes of this disclosure, specific activity is defined as follows: 1 U/mg of enzyme can convert 1 μmol of substrate per minute.

In addition, the invention relates to a process for preparing peptides and amino acids with N-terminal protection, of the general formula in which R' is a protective group or any amino acid or peptide residue which is attached by peptide or isopeptide linkage, and in which $R_2$ is a hydrogen or an alkyl and $R_1$ is a hydrogen or any side chain, and wherein enzymatic cleavage of the C-terminal amide group results in the formation of ammonia and either the amino acid with N-terminal protection or the free peptide as final products.

A process for eliminating the C-terminal amino group according to the present invention can be carried out continuously. In a preferred embodiment, this process is carried out with an immobilized enzyme according to the present invention in its native form or in a chemically or enzymatically modified form.

The enzymatic desamidation will be carried out at temperatures up to 40° C., usually at 30° C. in an aqueous or aqueous-organic medium using substrate concentrations >50 μM especially between 10 and 500 mM or above. The used specific activity of the enzyme depends upon the substrate used and will be usually between 2 and 100 U/mg (purified enzyme). The enzyme can be immobilized e.g. on Eupergit ® C. Some special procedures will be shown in the examples of the present specification. An example for continuously processing peptides will be shown Example 5.

Microbial production of a peptide amidase according to the present invention can be achieved in a known manner by genetic manipulation. In this regard, in an alternative method for producing a peptide amidase within the present invention, DNA encoding peptide amidase could be isolated and used, via known procedures, to transform a suitable host organism such that the enzyme is produced by the recombinant host in useful amounts. Peptide amidase-encoding DNA could be isolated by screening nucleic acid libraries generated from the species expressing a peptide amidase according to the present invention. See, e.g., Ausubel et al., CURRENT PROTOCOLS IN MOLECULAR BIOLOGY at 5 & 6, John Wiley and Sons, New York (1987, 1990) (hereafter "Ausubel"). Such libraries would be screened by means of oligonucleotide probes that are complementary to a polynucleotide encoding, for example, a portion of the N-terminus of a peptide amidase within the present invention.

Alternatively, other portions including or adjacent to the endogenous coding sequence of a peptide amidase according to the present invention can be used, when isolated using a probe as a template for generating other probes useful for isolating a peptide amidase-encoding polynucleotide according to the present invention. Such a probe could be used in a known manner to screen a genomic or cDNA library as described above, see Ausubel at §15.4.

A suitable polynucleotide in this regard would preferably comprise a nucleotide sequence, corresponding to the desired amino-acid sequence, that is optimized for the host of choice, as described below, with regard to codon usage, the initiation of translation, the most appropriate glycosylation pattern (if applicable), and the expression of recoverable amounts of a useful peptide amidase within the present invention. Also, a vector selected for transforming the chosen host organism with such a polynucleotide molecule should allow for efficient maintenance and transcription of the sequence encoding the polypeptide. Such a vector is readily available or derivable from commercial sources, and is suited to a particular host cell employed for expressing a peptide amidase according to the present invention. For vectors exemplary of those suitably used to the present invention, see Ausubel at §§2-4.

Host cells suitable for expressing a peptide amidase according to the present invention would include prokaryotic or eukaryotic cells, for example, bacterial, algal, yeast, insect, mammalian and human cells. Thus, among host cells suitable for the present invention would be microorganisms of the genera Aeromonas, Aspergillus, Bacillus, Escherichia, Kluyveromyces, Pichia, Rhodococcus, Saccharomyces and Streptomyces. More specifically illustrative of the suitable host microorganisms would be the bacteria *E. coli, B. subtilis* and *B. brevis*, as well as the yeast *S. cerevisiae* strain X2181-1B, with genotype a trp1 gal1 ade1 his2 (available from the Yeast Genetic Stock Center, Berkeley, Calif.); strain ATCC 52683, with genotype a his2 ade1 trp1 met14 ura3 (available from the American Type Culture Collection, Rockville, Md.); and strain ATCC 46183, with genotype a his1 trp1 (also available from the American Type Culture Collection). Host cells comprising a polynucleotide encoding a peptide amidase according to the present invention can be grown under conditions that provide expression of a peptide amidase of the present invention in recoverable amounts. See, e.g., Ausubel at §§1 & 13.

An economical process for the production of peptides according to the present invention is achieved by reacting optionally N-protected amino acids or peptide alkyl esters with amides of amino acids in an aqueous phase or an aqueous-organic medium with an enzyme capable of peptide linking preferably with a peptidase which results in peptidic linkage and the elimination of the amide protective groups from the product. In a preferred embodiment, the process is carried out continuously in which the resulting peptide is separated from the reaction mixture on the basis of its charge and the amide of the amino acid is recycled. In a particularly preferred embodiment, the process is carried out continuously in a device for the synthesis of dipeptides according to the present invention.

A process for the production of peptides according to the invention can be also be carried out in the presence of other enzymes in a one step complex enzymatic chain reaction. Particularly preferred enzymes are proteases, peptidases, esterases and lipases.

Further details are evident from the following description based on examples to illustrate the invention:

EXAMPLE 1

A. Preparation of the enzyme extract

A. Preparation of the enzyme extract

Flavedo was obtained by scraping 17 washed and newly harvested navel oranges. About 303.35 grams of flavedo was homogenized using both coarse and fine pestles in a 2.3% NaCl solution. During homogenization, the mortar containing the flavedo was cooled in ice. Peel residue was removed by centrifugation and filtration through paper filters.

B. Ammonium sulfate precipitation

The flavedo extract was then mixed with ammonium sulfate to achieve 30% saturation. Only a very small portion of the precipitate was protein in nature. The pH of the solution was 5.5 and was not adjusted. Most of the activity was located in 30–70% of the fraction. The precipitate was removed by centrifugation at 10,000 rpm for 25 min, and a concentrated solution in 50 mM tris/HCl, pH 7.5, was prepared. The volume was concentrated from 795 ml to 100 ml in this step (0.69 mg/ml protein to 2.91 mg/ml). Precipitation required about 3 hours.

C. Gel chromatography with Sephadex ® G-10

In this step, the protein solution buffer was replaced with 50 mM tris, pH 7.5, with simultaneous removal of low molecular weight constituents which appear as a fluorescent yellow band. Gel chromatography was carried out under the following conditions:
Column 26.5×5 cm (520 ml), equilibrated with 50 mM tris/HCl; pH 7.5
Flow rate: 1.66 ml/min
Sample volume: 50 ml (147 mg of protein, 59.1 U); substrate: Z-GLy-Tyr-NH$_2$ (compare Example 1E).
The enzyme extract in 150 ml of tris buffer was then concentrated with an Amicon spiral ultrafiltration membrane (YM 2000) to 52 ml. The concentrated extract was used for the ion exchange chromatography.

D. Ion exchange chromatography with Sephadex ® A-50

Fifty-two milliliters of the concentrated G-10 fraction prepared according to Example 1C above were pumped onto the column. The peptide amidase was eluted with the flow-through protein peak as a clear colorless solution. Ion exchange chromatography was carried out under the following conditions
Column: 16.5×5 cm (324 ml)
Flow rate: 0.4 ml/min
Sample volume: 52 ml (88.2 mg of protein) with 25 mM tris/HCl, pH 7.5.

Figure 1:
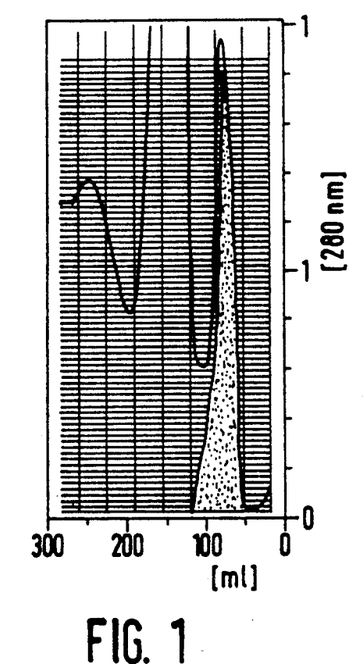
FIG. 1 shows an ion exchange chromatogram of purified peptide amidase.

The results of a representative chromatogram with DEAE-Sephadex ® A-50 are shown in FIG. 1. Results of the purification steps are listed in Table 2.

TABLE 2

|  | Volume [ml] | Protein [mg/ml] | Total protein [mg] | Activity [U/mg] | Total activity [U] |
|---|---|---|---|---|---|
| Extract | 795 | 0.694 | 552 | 0.355 | 196 |
| Fraction (NH$_4$)$_2$SO$_4$ | 100 | 2.94 | 294 | 0.402 | 118 |
| G-10 | 300 | 0.795 | 238 | 0.43 | 103 |
| G-10 (UF) | 100 | 1.69 | 170 | 0.59 | 103 |
| IEC A-50 | 174 | 0.16 | 27.8 | 1.65 | 45.6 |
| IEC A-50 (UF) | 28 | 0.80 | 22.6 | 1.63 | 45.52 |

G-10: Change of buffer with Sephadex ® G-10
IEC: Ion exchange chromatography on DEAE Sephadex ® A-50
UF: Ultrafiltration
Fraction: 30–70% (NH$_4$)$_2$SO$_4$ In nature the peptide amidase is present in the flavedo of citrus fruits associated with other proteins or enzymes catalyzing other reactions especially cleaving peptide bonds. The substrate spectrum of the inventive peptide amidase in the naturally occuring mixture would be considerably restricted. By isolation of the enzyme from natural material, disturbing side reactions are eliminated and, by further purification, higher specific activities are obtained, permitting an economical employment of the enzyme.

E. Determination of enzyme activity

Z-Gly-Tyr-NH$_2$ was used as a substrate although considerably higher activities were measured with other substrates, such as H-Tyr-Arg-NH$_2$. For the purposes of this invention, Z is a benzyloxycarbonyl protecting group. Peptides with free N-terminals were rapidly hydrolyzed by proteases present in the mixture at the start of purification, whereas Z-Gly-Tyr-NH$_2$ was not cleaved. This substrate proved suitable for determining enzyme activity even in unpurified extracts because complete separation by HPLC was possible in 6–8 minutes at 280 nm (few interfering factors).

The following reaction mixture was employed:

| 100 mM | Z-Gly-Tyr-NH$_2$ in H$_2$O/ethanol (1:1) | 0.1 ml |
|---|---|---|
| 0.8 mg/ml | enzyme solution | 0.05–0.3 ml |
| 0.05M | tris/HCl, pH 7.5 | 0.85–0.6 ml |

At various times, 0.1 ml of the reaction solution was pipetted into glacial acetic acid (1:1) in order to stop the reaction. The amount of Z-Gly-Tyr-OH formed was determined quantitatively by HPLC. A calibration plot of the integrated areas was used to calculate the amount of Z-Gly-Tyr-OH formed at 5 time points. The rate of reaction rate was determined by measuring the increase in Z-Gly-Tyr-OH.

Separation was carried out on an ODS-Hypersil 5μ RP-18 column with tetrabutylammonium bisulfate (0.1M)/acetonitrile (65/35) at 0.1 ml/minute employed as the eluent.

| Retention times: | Z-Gly-Tyr-NH$_2$: | 4.5 (substrate) |
|---|---|---|
|  | Z-Gly-Tyr-OH: | 5.9 (product) |

The activity was determined to be 2–4 U/mg of protein (purified enzyme) with the substrate Z-Gly-Tyr-NH$_2$.

In addition to the peptide amidase, the protein extract also contained carboxypeptidase prior to the step preceding ion exchange chromatography. The mixture of these two enzymes can be used for the stepwise synthesis of peptides by coupling an amide of amino acid and amide cleavage according to the methods described in Example 6.

EXAMPLE 2

Characterization of the enzyme

A. pH-Dependence of the activity

The reaction rate for the cleavage of the amide group of benzyloxycarbonyl-glycyltyrosinamide (Z-Gly-Tyr-NH$_2$) was determined as a function of the pH of the reaction mixture. The following assay mixture was employed:

| | | |
|---|---|---|
| 100 mM | Z-Gly-Tyr-NH$_2$ in water/ethanol (1:1) | 0.1 ml |
| 0.17 mg/ml | enzyme solution | 0.3 ml |
| 0.1M | buffer | 0.6 ml |

Before the start of the reaction, the pH was adjusted to various values in the range pH 4.0–5.5 in citrate buffer, pH 6.0–8.5 in potassium phosphate buffer and pH 9.0–10.0 in sodium carbonate buffer by adding sodium hydroxide or hydrochloric acid. A peptide amidase according to the present invention was incubated in a buffer solution at 30° C. for 15 minutes. After the reaction was initiated by the addition of substrate, the pH was determined. After intervals of 30 minutes, 1 hour and 2 hours, the reaction in aliquots of the mixtures was stopped by the addition of 1:1 glacial acetic acid according to the method described in Example 1.

Figure 2:
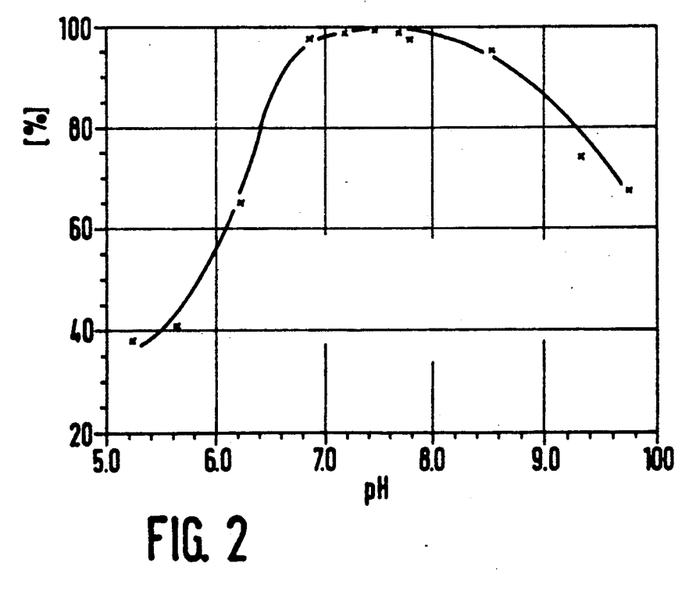
FIG. 2 shows the activity of peptide amidase as a function of pH.

Peptide amidase according to the present invention was active over the relatively wide pH range of 6–9. At pH 10, the enzyme exhibited 65% of the activity measured at optimum pH (see FIG. 2).

B. Dependence of peptide amidase activity and stability on reaction temperature Assay mixtures containing 10 mM Z-Gly-Tyr-NH$_2$ in 50 mM tris/HCl buffer, pH 7.5, were initially equilibrated at temperatures between 11° C. and 56° C. The reaction was initiated by the addition of an enzyme solution. A reaction mixture according to Example 2A was employed. At various time intervals, aliquots of the reaction mixtures were pipetted into cooled glacial acetic acid and analyzed by HPLC, and the activity was determined from the gradient in the linear region.

To determine the stability as a function of the temperature, peptide amidase within the present invention was preincubated in buffer at particular temperatures for 10, 30, 65, 115, 171, 235 and 310 minutes. The reaction was initiated by the addition of substrate and the activity was measured. No loss in enzyme activity was measured at 25° C. to 30° C. for the entire incubation period up to 310 minutes. Moreover, the enzyme was employed in an enzyme membrane reactor for several days at 22° C. (room temperature) without any loss of activity.

TABLE 3

Figure 3:
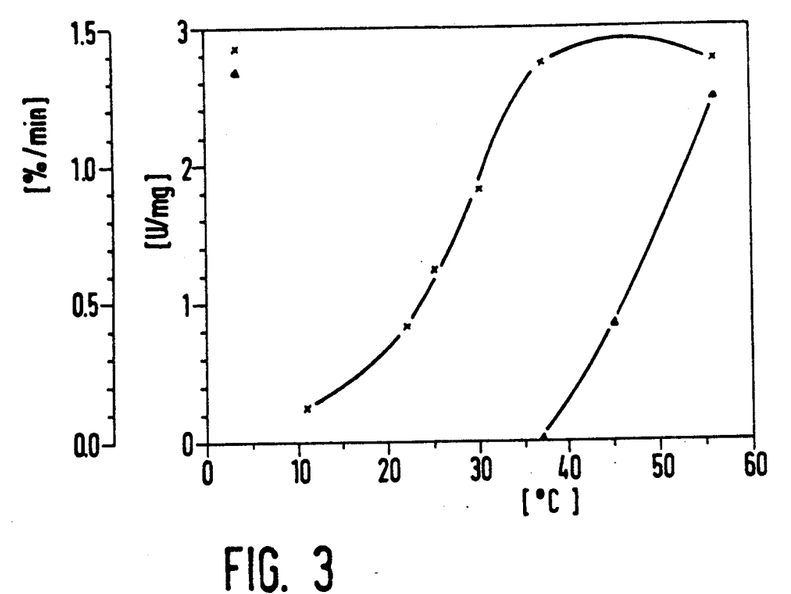
FIG. 3 shows the activity of peptide amidase as a function of temperature.

Activity and inactivation rate of peptide amidase as a function of the temperature (see Fig. 3)

| Temperature [°C.] | Specific Activity [U/mg] | Inactivation rate [%] | Inactivation rate [%/min] |
|---|---|---|---|
| 11 | 0.26 | 9.3 | |
| 22 | 0.84 | 30.4 | |

TABLE 3-continued

Activity and inactivation rate of peptide amidase as a function of the temperature (see Fig. 3)

| Temperature [°C.] | Specific Activity [U/mg] | Inactivation rate [%] | Inactivation rate [%/min] |
|---|---|---|---|
| 25 | 1.25 | 45.2 | |
| 30 | 1.83 | 66.2 | |
| 37 | 2.74 | 98.9 | 0.015 |
| 56 | 2.77 | 100 | 1.35 |

C. Effect of chelating agents, metal cations and enzyme inhibitors on peptide amidase activity The effect of the following inhibitors on peptide amidase activity was determined under standard conditions according to the methods described in Example 1. The inhibitor concentration was 10 mM in each case. The results are presented in Table 4 which shows that only PMSF significantly inhibited enzyme activity.

TABLE 4

Action of various effectors on the peptide amidase activity

| Inhibitor [0.01 m] | % activity remaining |
|---|---|
| Complexing agents: | |
| NaN$_3$ | 100% |
| EDTA | 92% |
| PLP enzyme inhibitors: | |
| Cycloserine | 100% |
| Semicarbazide | 102% |
| Serine hydrolase inhibitors: | |
| PMSF | 55% |
| Others: | |
| Cycloheximide | 98% |
| Glycine | 99% |
| Dithiothreitol | 100% |
| SH-group reagents: | |
| p-OHMBA | 96% |
| Iodoacetamide | 99% |
| EMI | 100% |
| HgCl$_2$ | 95% | p-OHMB: para-hydroxymercuribenzoate
EMI: ethylmaleimide
PMSF: phenylmethanesulfonyl fluoride
EDTA: ethylenedinitrilotetraacetic acid

D. Stability of peptide amidase

The activity of the peptide amidase was measured after storage for a period of several months under various conditions. The enzyme solution prepared according to the method described in Example 1C was stored under the following conditions:

- in sterile 0.1M citrate buffer, 50 mM KPi added, pH 7.5 in a sterile bottle at 4° C. and protected from light
- identical solution frozen at −20° C. without additives
- 30–80% (NH$_4$)$_2$SO$_4$ solution desalted on G-10 columns (2.5 ml) shortly before activity measurement (buffer: 50 mM KPi, pH 7.5)

The reaction rate was measured after 1, 5, 12, 17, 38 and 124 days. No loss of activity was found in any of these solutions over this time period. The enzyme could also be stored in its purified form, as described in Example 1D, at 4° C. for several weeks without any measurable loss of activity. The purified enzyme could be lyophilized as well.

E. Determination of Molecular weight

The molecular weight of a peptide amidase according to the present invention was determined by SDS-PAGE electrophoresis by the Lämmli method. A portion of the sample was mixed with 10% mercaptoethanol in order to determine the molecular weight of subunits. The molecular weight of the unreduced enzyme was determined as 23,000+/−3000 daltons from samples without added mercaptoethanol. A standard protein calibration curve was used for this determination (Boehringer Mannheim). The SDS-PAGE electrophoresis was carried out under the following conditions:
gel: 20% (10%) running gel, 2% collecting gel;
electrophoresis chamber: Bio-Rad Protean TM II with Desatronic 3000/200 (Desaga, Heidelberg) power supply;
Running conditions: 80 V (15 mA) in the collecting gel, 200 V (35 mA) in the running gel;
staining: Coomassie Blue.
Sometimes aggregates are formed having a molecular weight of approximately 160,000 daltons.

Example 3

Substrate spectrum of the peptide amidase

A. Stereospecificity of the enzyme for various peptide derivatives containing D-amino acids

TABLE 5

Deamidation of tripeptides containing D-amino acids

| Substrate | Product | Conversion (%/12 hours) |
| --- | --- | --- |
| H-Gly-D-Phe-Tyr-NH$_2$ | H-Gly-D-Phe-Try-OH | 100 |
| H-Gly-Phe-D-Phe-NH$_2$ | H-Gly-Phe-D-Phe-OH | 0 |
| H-Arg-Pro-D-Ala-NH$_2$ | H-Arg-Pro-D-Ala-OH | 0 |

Separate conditions:
Column: RP 18, 0.1 ml/min
Eluent: Solution of TBA (tetrabutylammonium hydrogen sulfate) and acetonitrile
Detection: 256 nm

B. Cleavage of N-terminal protected amino acid amides

TABLE 6

| Deamidation of N-terminal protected amino acid amides | |
| --- | --- |
| Amide | Yield after 45 min (%) |
| Bz-Tyr-NH$_2$ | 47.6* |
| Z-Trp-NH$_2$ | 14.9 |
| Ac-Trp-NH$_2$ | 48.9 |
| Bz-Arg-NH$_2$ | 73.5 |

*yield after 15 minutes

Separating conditions according to Example 3A were employed.
Eluent: TBA/acetonitrile 65:35 (90:10 for Bz-Arg-NH$_2$)
Bz: N-benzyl protecting group
Ac:

TABLE 6A

| Enzymatic reaction of amino acid amides with protected α-amino function | | | | |
| --- | --- | --- | --- | --- |
| Substrate | Product | Spec. Activity (U/mg) | Yield (%/28 min) | Yield (%/2 h) |
| Bz-Tyr-NH$_2$ | Bz-Tyr-OH | 6.34 | 88.7 | 100 |
| Z-Trp-NH$_2$ | Z-Trp-OH | 0.37 | 5.16 | 23.5 |
| Ac-Trp-NH$_2$ | Ac-Trp-OH | 2.32 | 32.4 | 100 |
| Bz-Arg-NH$_2$ | Bz-Arg-OH | 4.39 | 61.6 | 100 |

Reaction conditions: 10 mM substrate; 50 μg.ml peptide amidase; 50 mM tris/HCl; pH 7.0;
Temperature 30° C.

C. Cleavage of amides of peptides and amino acids with N-terminal protection

TABLE 7

| Enzymatic cleavage of N-terminal protected dipeptide amides | | | |
| --- | --- | --- | --- |
| Protected dipeptide amides | Retention times (60/40) | | Yield (%) |
| | Dipeptide | Dipeptide amide | |
| Z—Gly—Phe—NH$_2$ | 10.1 | 6.8 | 100 |
| Z—Pro—Phe—NH$_2$ | 15.1 | 11.1 | 100 |
| Z—Gly—Tyr—NH$_2$ | 5.2 | 4.2 | 100 |
| Bz—Tyr—Thr—NH$_2$ | 3.5 | 3.1 | 63 |
| Bz—Tyr—Val—NH$_2$ | 6.0 | 4.3 | 100 |
| Bz—Tyr—Ile—NH$_2$ | 5.4 | 5.2 | 100 |
| Bz—Tyr—Ser—NH$_2$ | 3.4 | 3.0 | 41 |
| Bz—Tyr—Trp—NH$_2$ | 9.7 | 6.6 | 39 |
| Bz—Tyr—Ala—NH$_2$ | 4.0 | 3.3 | 65 |
| Bz—Tyr—Leu—NH$_2$ | 6.2 | 4.6 | 100 |
| Bz—Tyr—NH$_2$ | 9.24 | 21.2 | 100 |
| Boc—Leu—Val—NH$_2$ | 11.4 | 7.1 | 20 |
| Trt—Gly—Leu—Val—NH$_2$ | 3.6 | 10.6 (80/20) | 95 |
| Z—Pro—Leu—Gly—NH$_2$ | 4.9 | 6.3 | 90 |
| Z—Gly—Gly—Leu—NH$_2$ | 3.9 | 5.0 | 100 |
| Bz—Tyr—Lys—NH$_2$ | | Bz—Tyr—Lys—OH | 100 |
| For—Tyr—Arg—NH$_2$ | → | For—Tyr—Arg—OH | 100 |
| Mal—Tyr—Arg—NH$_2$ | | Mal—Tyr—Arg—OH | 100 |
| Z—Arg—Arg—pNa (comparison) | | No reaction in 12 h | | pNa: para-nitroanilide
Boc: tert-Butyloxycarbonyl protecting group
Trt: triphenylmethyl protecting group
For: formyl protecting group
Mal: maleimide protecting group The results in Table 7 were obtained using an eluent: TBA/acetonitrile 60/40 (% volume)

D. Cleavage of peptide amides with free N termini

Enzyme activity measured for the deamidation of dipeptide amides with free N termini (e.g. H-Tyr-Arg-NH$_2$) was considerably higher than for peptide amides with an aromatic protective group, such as Z- or Bz-. Activity levels were up to 100 times higher than those measured with protected peptide amides. The results are presented in Table 8a and 8.

TABLE 8a

Amides of amino acid side chains (Asn; Gln)
Analysis by amino acid analyzer

| Amide | Acid | Retention Time Amide | Acid | Conversion (%) |
|---|---|---|---|---|
| H—Ala—Asn | H—Ala—Asp | 37.3 | 33.2 | 0 |
| H—Ala—Gln | H—Ala—Glu | 38.2 | 39.5 | 0 |
| H—Leu—Arg—Asn | H—Leu—Arg—Asp | 53.0 | —* | 0 |

*no reference available

TABLE 8

Enzymatic cleavage of the acid amide group of dipeptide amides without N-terminal protection using a peptide amidase purified from orange flavedo

| Unprotected peptide amides | Retention times | |
|---|---|---|
| | Peptide amide | Free peptide |
| H—Tyr—Arg—NH$_2$ | 2.81 | 3.0 * |
| H—Tyr—Lys—NH$_2$ | 2.8 | 3.0 * |
| H—Tyr—Ser—NH$_2$ | 2.9 | 3.1 * |
| H—Phe—Arg—NH$_2$ | 2.8 | 3.2 |
| H—Phe—Lys—NH$_2$ | 2.8 | 3.2 |
| H—Phe—Ser—NH$_2$ | 3.1 | 4.5 |
| H—Trp—Arg—NH$_2$ | 3.4 | 3.9 |
| H—Trp—Lys—NH$_2$ | 3.2 | 4.0 |
| H—Trp—Ser—NH$_2$ | 4.0 | 4.8 |
| H—Val—Phe—NH$_2$ | 11.54 | 27.3 |
| H—Asp—Phe—NH$_2$ | 12.12 | 12.9 |
| H—Ala—Phe—NH$_2$ | 4.8 | 8.1 |
| H—Arg—Met—NH$_2$ | 6.7 | 5.4 |
| H—Phe—Leu—NH$_2$ | 17.5 | 22.1 |

The yield was 95–100% in each case
Eluent (HPLC): TBA/acetonitrile 95/5 or 96/4(*)
Reaction conditions: 10 mM substrate; 50 µg/ml peptide amidase; 50 mM tris/HCL; pH 7.0; temperature 30° C.

E. Amides of amino acids

The results in Table 9 show that of the amino acid amides tested, none was deamidated. These results clearly indicate that the enzyme is specific for peptide amides. A DEAE-purified enzyme was employed in these experiments (volumetric activity: 40 U/ml for the substrate For-Tyr-Arg-NH$_2$).

TABLE 9

Cleavage of amides of amino acids using a peptide amidase from orange flavedo. (50 µg/ml; 10 mM substrate)

| Amino acid** (amide of AA) | RF of amide | RF of AA | Reaction |
|---|---|---|---|
| Ala—NH$_2$ | 0.47 | 0.33 | 0 |
| Arg—NH$_2$ | 0.18 | 0.08 | 0 |
| Leu—NH$_2$ | 0.76 | 0.63 | 0 |
| Tyr—NH$_2$ | 0.71 | 0.59 | 0* |
| Met—NH$_2$ | 0.70 | 0.56 | 0 |
| Phe—NH$_2$ | 0.75 | 0.64 | 0* |
| Lys—NH$_2$ | 0.12 | 0.08 | 0 |
| Val—NH$_2$ | 0.67 | 0.57 | 0 |
| Ile—NH$_2$ | 0.72 | 0.65 | 0 |
| His—NH$_2$ | 0.17 | 0.11 | 0 |
| Thr—NH$_2$ | 0.45 | 0.35 | 0 |
| Trp—NH$_2$ | 0.76 | 0.67 | 0 |
| Ser—NH$_2$ | 0.32 | 0.16 | 0 |
| D—Phe—NH$_2$ | 0.75 | 0.64 | 0 |
| D—Ala—NH$_2$ | 0.46 | 0.33 | 0 |
| D—Leu—NH$_2$ | 0.75 | 0.63 | 0 |

*slight traces
**unprotected α-amino function

Eluent: pyridine/butanol/AcOH/H$_2$O (12:15:3:5).

Reaction: 24 h, RT; 0.05M KPi, pH 7.5., 30° C.
Blank sample without enzyme.

EXAMPLE 4

Effect of organic solvents on the enzyme activity and stability

A. Concentration-dependence of the activity

The effect on enzyme activity of the concentration of a peptide amidase according to the present invention in water-soluble solvents such as ethanol, propanol, DMF and acetone was investigated. A reaction mixture comprising the following constituents was employed:
850 µl of the particular solvent/tris (50 mM; pH 7.5) mixture
100 µl of substrate (10 mM Z-Gly-Tyr-NH$_2$)
50 µl of amidase (40 µg of protein)

Figure 4:
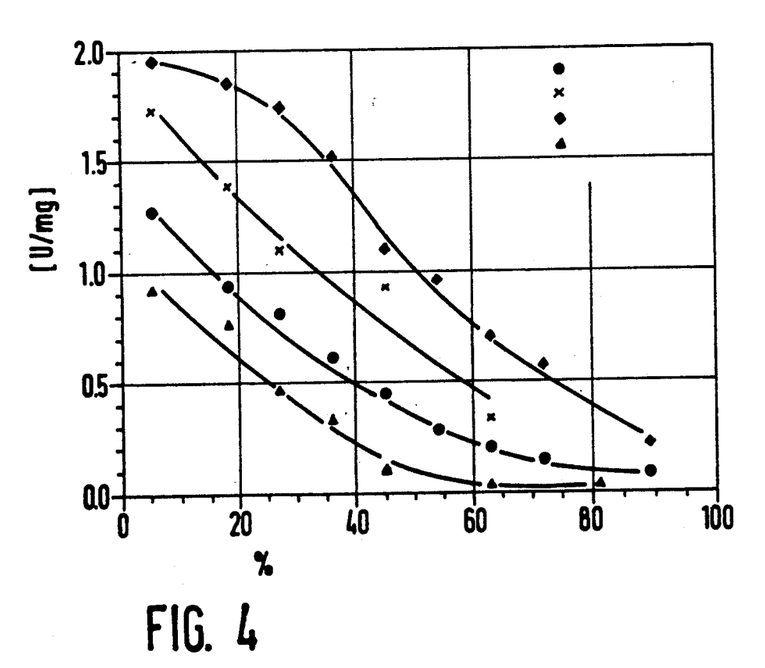
FIG. 4 depicts the activity of peptide amidase as a function of its concentration in water-soluble solvents.

The reaction was initiated by the addition of the enzyme to prevent inactivation of the enzyme prior to the reaction. The results are presented in Table 10 and FIG. 4.

TABLE 10

Effect on Enzyme Activity as a function of the concentration of peptide amidase in water-soluble solvents

| Conc. of the solv. | Activity [U/mg] | | | |
|---|---|---|---|---|
| | Acetone | DMF | Ethanol | Propanol |
| 89.1% | 0.224 | 0 | 0.083 | 0.05 |
| 72.0% | 0.585 | 0 | 0.149 | 0.1 |
| 63.0% | — | 0.195 | 0.204 | 0.1 |
| 54.0% | — | 0.777 | 0.284 | 0.1 |
| 45.0% | 1.38 | 0.931 | 0.448 | 0.12 |
| 36.0% | 1.527 | — | 0.613 | 0.342 |
| 27.0% | 1.748 | 1.099 | 0.814 | 0.474 |
| 18.0% | 1.863 | 1.391 | 0.938 | 0.772 |
| 5.0% | 2.011 | 1.727 | 1.269 | 0.927 |

B. Effect of the solvent concentration on Km and Vmax

TABLE 11

Effect of the acetone concentration in the mixture on kinetic parameters

| Concentration (Acetone) | Km [mM] | Vmax [U/mg] |
|---|---|---|
| 5% | 0.063 | 2.93 |
| 20% | 1.6 | 2.54 |
| 40% | 5.5 | 2.57 |
| 60% | 19.6 | 2.58 |

Substrate: Z-Gly-Tyr-NH$_2$; 40 µg/ml peptide amidase in 50 mM tris/HCl, pH 7.5

Similar effects were observed with DMF as a solvent. $K_m$ and $V_{max}$ did not vary significantly when the more polar substrate Bz-Arg-NH$_2$ was used.

C. Effect on stability

Figure 5:
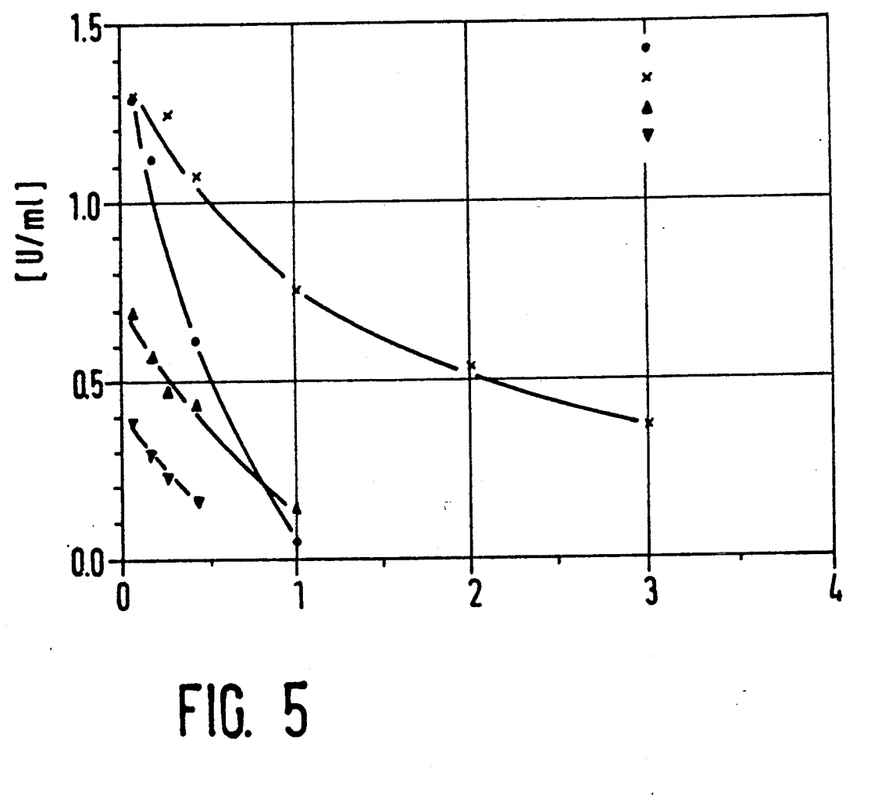
FIG. 5 compares the stability of the enzyme as a function of its solvent.

Solvents:
Acetone
Acetonitrile
DMF
Ethanol
30% solvent in each mixture
Incubation with 27.8% solvent Ten identical mixtures of the following composition:
250 µl of solvent
600 µl of 50 mM tris/HCl, pH 7.5
50 µl of enzyme solution (40 µg of protein/mixture) were incubated at 30° C. At various times, the reaction was initiated by the addition of substrate (Z-Gly-Tyr- NH₂ in 100 μl of buffer/solvent 1:1, corresponding to 10 mM/mixture) and the activity was measured. The results are shown in FIG. 5.

These results show that the smallest decrease in enzyme activity was found with dimethylformamide. The peptide amidase still exhibited 28.5% of its initial activity after incubation with 27.8% DMF at 30° C. for 2 days.

EXAMPLE 5

Continuous deamidation of H-Tyr-Arg-NH₂ in an enzyme membrane reactor (EMR) and preparation of the reaction solution A continuous process for deamidation of H-Tyr-Arg-NH₂ was carried out in an EMR. The conditions for operating the EMR (corresponding to a continuously operated stirred vessel reactor) permitted a more economic utilization of the enzyme because the enzyme was removed by ultrafiltration before the product was purified. The process was carried out under the following conditions:

| Tyr—Arg—NH₂: | 20 mM |
|---|---|
| Residence time: | 30 minute |
| Enzyme concentration: | 0.15 mg/ml |
| Mean conversion: | 92% |
| Space-time yield: | 192.5 g/(L × d) |

The reaction solution was then purified by anion exchange chromatography. The remaining peptide amide was not bound and could be recycled, while the deamidated peptide was bound and was eluted by a salt gradient as follows:

| Column: | 2.4 × 10 cm |
|---|---|
| Column material | Dowex 1 × 4; 200–400 mesh |
| Eluent: | Tris/HCl; pH = 9.0; Gradient 0–40% 1 M NaCl |

Figure 7:
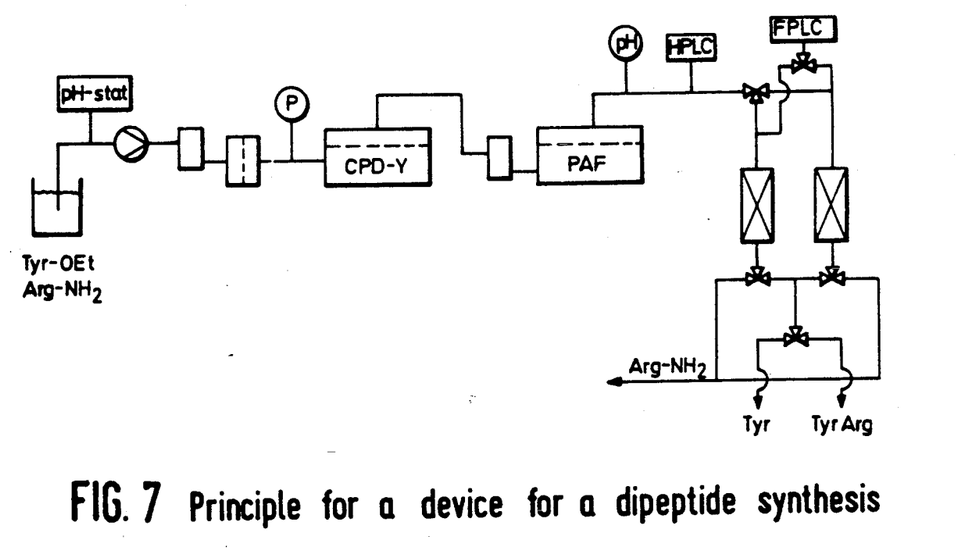
FIG. 7 presents a schematic diagram of a device for the synthesis of dipeptides according to the present invention.

The dipeptide H-Tyr-Arg-OH was eluted between 6 and 9% using a 1 molar NaCl solution. FIG. 7 of the drawings shows a scheme for a device.

EXAMPLE 6

Figure 6:
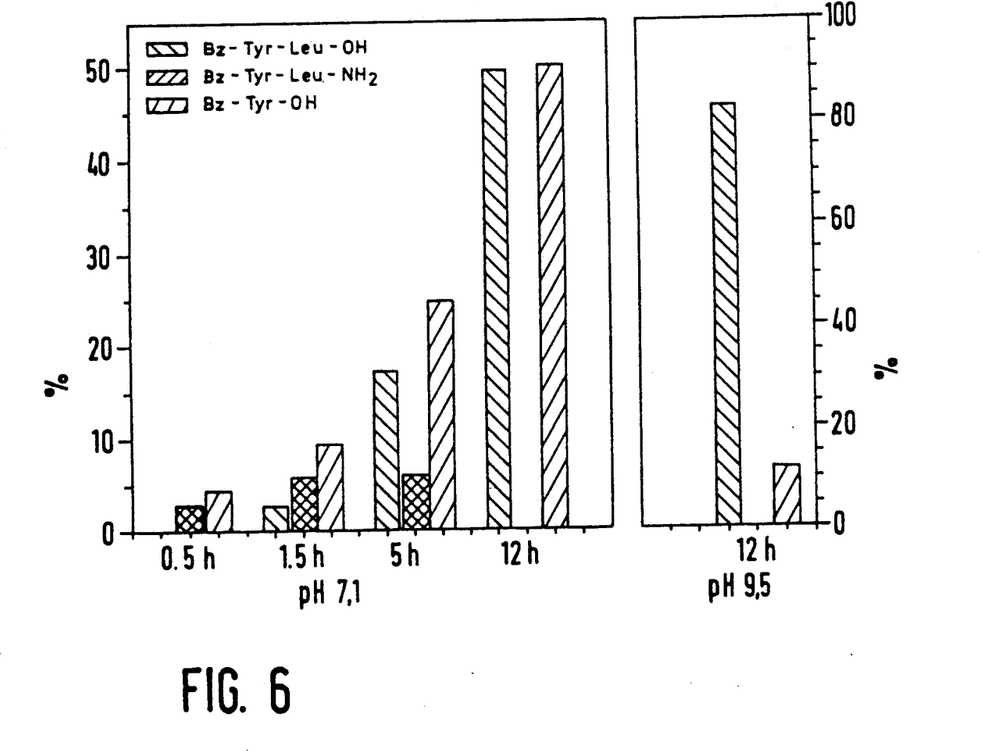
FIG. 6 shows the percentage of end products produced over time as the result of a process of simultaneous deamidation of peptide amides and peptide synthesis.

Simultaneous elimination of the amide group from the peptide amide and enzymatic peptide synthesis using a peptide amidase An enzyme preparation containing both carboxypeptidase C (Zuber, H., Hoppe Seyler's Z. Phys. Chem. 1968, 349, 1337–1352) and a peptide amidase (PAF) according to the present invention was used for the enzymatic synthesis of the dipeptide Bz-Tyr-Leu-NH₂ (Steinke, D., Kula, M. R., Enz. Microb. Technol., 1990, p. 836–40). The end product was a dipeptide, Bz-Tyr-Leu-OH without C-terminal protection (FIG. 6). The reaction mixture contained:

36 mM Bz-Tyr-OEt
225 mM H-Leu-NH₂
0.2M sodium phosphate buffer, pH 7.1
300 μl of enzyme preparation (0.37 mg of protein/mixture)

The resulting products were identified by HPLC and amino acid analysis as shown in FIG. 6. Additional results of these experiments are presented in Table 12.

TABLE 12

Enzymatic reaction of peptide amides with a chain length of greater than three amino acids. Reaction conditions: 10 mM substrate, 40 μg/ml peptide amidase, 50 mM tris/HCL, pH 7.0, temp. 30° C.

| Substrate | Product | Yield [%/6 h] |
|---|---|---|
| Trt—Gly—Leu—Val—NH₂ | Trt—Gly—Leu—Val—OH | 100 |
| Z—Pro—Leu—Gly—NH₂ | Z—Pro—Leu—Gly—OH | 100 |
| Z—Gly—Gly—Leu—NH₂ | Z—Gly—Gly—Leu—OH | 100 |
| Z—Pro—Arg—Gly—NH₂ | Z—Pro—Arg—Gly—OH | 100 |
| H—Pro—Arg—Gly—NH₂ | H—Pro—Arg—Gly—NH₂ | 100 |
| VP-Antagonist | VP-Antagonist (free acid) | 100 |
| Boc—cys(bzl)—Pro—Arg—Gly—NH₂ (SEQ. ID. NO. 1) | Boc—cys(bzl)—Pro—Arg—Gly—NH₂ (SEQ. ID. NO. 1) | 90 |
| H—Tyr—Gly—Gly—Phe—Leu—NH₂ (SEQ. ID. NO. 2) | H—Tyr—Gly—Gly—Phe—Leu—OH (SEQ. ID. NO. 2) | 100 |
| LHRH | LHRH (free acid) | 90 |
| Z—Val—Gly—Ala—Pro—NH₂ (SEQ. ID. NO. 3) | Z—Val—Gly—Ala—Pro—NH₂ (SEQ. ID. NO. 3) | 0 |

VP-Antagonist: Vasopressin Antagonist (9 Amino acids with internal disulfide bonds)
H—tyr—Gly—Gly—Phe—Leu—NH₂: (SEQ. ID. NO. 2) Leu-Enkephalin
LHRH: Luteinizing Hormone Releasing Factor

EXAMPLE 7

The effect of pH on the stability of peptide amidase

One hundred microliters of a peptide amidase solution (concentration 0.172 mg/ml) and 100 μl of 10 mM ammonium carbonate buffer, pH 6–9, were mixed and incubated at room temperature. To determine the effect of pH on stability of the enzyme, the activity of ten microliter aliquots was measured at specific time intervals using H-Tyr-Arg-NH₂ as the substrate. The results show that no noticeable decrease in activity takes place over a period of 190 hours.

The assay conditions were as follows:
Substrate: 19 mM H-Tyr-Arg-NH₂
pH: 7.5
Volume: 20 μl
Enzyme: 0.0086 mg/ml
Incubation time: 30 minute

EXAMPLE 8

Effect of various materials on the stability of peptide amidase

The compatibility of a peptide amidase according to the present invention with certain materials was investigated by adding small pieces of the material to a solution containing 100 μl of the enzyme (concentration 0.172 mg/ml) and 100 μl of 10 mM ammonium carbonate buffer. The solution was then incubated at room temperature at pH 7.5. Aliquots of the solution were tested at specific time intervals for enzyme activity. Enzyme activity was measured according to the method described in Example 1E.

Polypropylene, Teflon, rubber (O ring), silicone, V4A steel and plexiglass were investigated. No noticeable decrease in peptide amidase activity was observed with any of the materials tested. No important differences were detected.

The inventive enzymatic desamidation is also used for the removal of the amide bond of peptide amides synthesized by conventional chemical methods e.g., by Merrifield solid phase synthesis, where the production of amides is for the most part, more simple than the synthesis of acids.

What is claimed is:

1. A peptide amidase which can be isolated from the flavedo of citrus fruits and that catalyzes the selective hydrolytic elimination of the free amino group at the C-terminal location of peptide amides, and wherein said amidase, in substantially pure form, (A) is further capable of catalyzing the elimination of the C-terminal amino group of N-terminal protected amino acid amides;
(B) does not cleave peptide bonds;
(C) has an optimum pH of 7.5+/−1.5;
(D) is stable at pH 6.0-9.0;
(E) has an optimum temperature of 30° C. at pH 7.5;
(F) exhibits weak inhibition by serine protease inhibitors;
(G) has a molecular weight of 23,000+/−3000 daltons as measured by electrophoresis;
(H) has an isoelectric point of pH 9.5; and
(I) is liable to aggregation.

2. A peptide amidase according to claim 1, wherein said flavedo is obtained from oranges.

* * * * *